(12) United States Patent
Parizot

(10) Patent No.: US 7,662,117 B2
(45) Date of Patent: Feb. 16, 2010

(54) SPLINT FOR A JOINT CONNECTION AND METHODS FOR PRODUCTION OF SUCH A SPLINT

(76) Inventor: Jean-Paul Parizot, 17, Place Darcy, Dijon (FR) F-21000

( * ) Notice: Subject to any disclaimer, the term of this patent is extended or adjusted under 35 U.S.C. 154(b) by 729 days.

(21) Appl. No.: 10/511,377

(22) PCT Filed: Apr. 15, 2003

(86) PCT No.: PCT/FR03/01207

§ 371 (c)(1),
(2), (4) Date: Jul. 11, 2005

(87) PCT Pub. No.: WO03/086248

PCT Pub. Date: Oct. 23, 2003

(65) Prior Publication Data

US 2006/0004310 A1    Jan. 5, 2006

(30) Foreign Application Priority Data

Apr. 15, 2002    (FR) .................................... 02 05352

(51) Int. Cl.
*A61F 5/00* (2006.01)
(52) U.S. Cl. ................. 602/5; 602/13; 602/27
(58) Field of Classification Search ........ 602/5, 602/13, 20, 21–23, 26–27, 60–62; 128/882, 128/DIG. 20
See application file for complete search history.

(56) References Cited

U.S. PATENT DOCUMENTS

| 4,628,945 | A | * | 12/1986 | Johnson, Jr. | ............. 602/27 |
| 4,661,535 | A | | 4/1987 | Borroff et al. | |
| 5,007,416 | A | | 4/1991 | Burns et al. | |
| 5,027,801 | A | | 7/1991 | Grim | |
| 5,445,602 | A | * | 8/1995 | Grim et al. | ............. 602/27 |
| 5,695,452 | A | | 12/1997 | Grim et al. | |

(Continued)

FOREIGN PATENT DOCUMENTS

FR    2721037    12/1995

(Continued)

*Primary Examiner*—Michael A. Brown
(74) *Attorney, Agent, or Firm*—Blakely, Sokoloff, Taylor & Zafman

(57) ABSTRACT

The invention relates to a splint for a joint connecting two parts of a human body or of an animal, such as the ankle, knee or elbow for example, comprising at least one rigid shell (1,2), globally concave, for positioning around the joint in order to support said joint. The splint comprises, on the internal face thereof, in other words the concave face, a chamber (3,4) made from a flexible plastic material which may be placed under pressure by any suitable means, and positioned on the internal face of the shell (1,2) to provide a supportive cushion between said shell (1, 2) and the joint and covering at least a part of the internal face of the shell (1,2). The splint comprises means (6) for holding said shell (1,2) in position about the joint, characterized in that the shell (1,2) is made from a single element comprising at least one flexible zone (7, 8;12, 13) made from a styrene ethylene butylene styrene block copolymer (SEBS), chemically bonded to the rigid part of the shell (1,2) to avoid any injury to the oedematic tissue which appears after a sprain or strain of said joint.

22 Claims, 5 Drawing Sheets

U.S. PATENT DOCUMENTS

Figure 4:
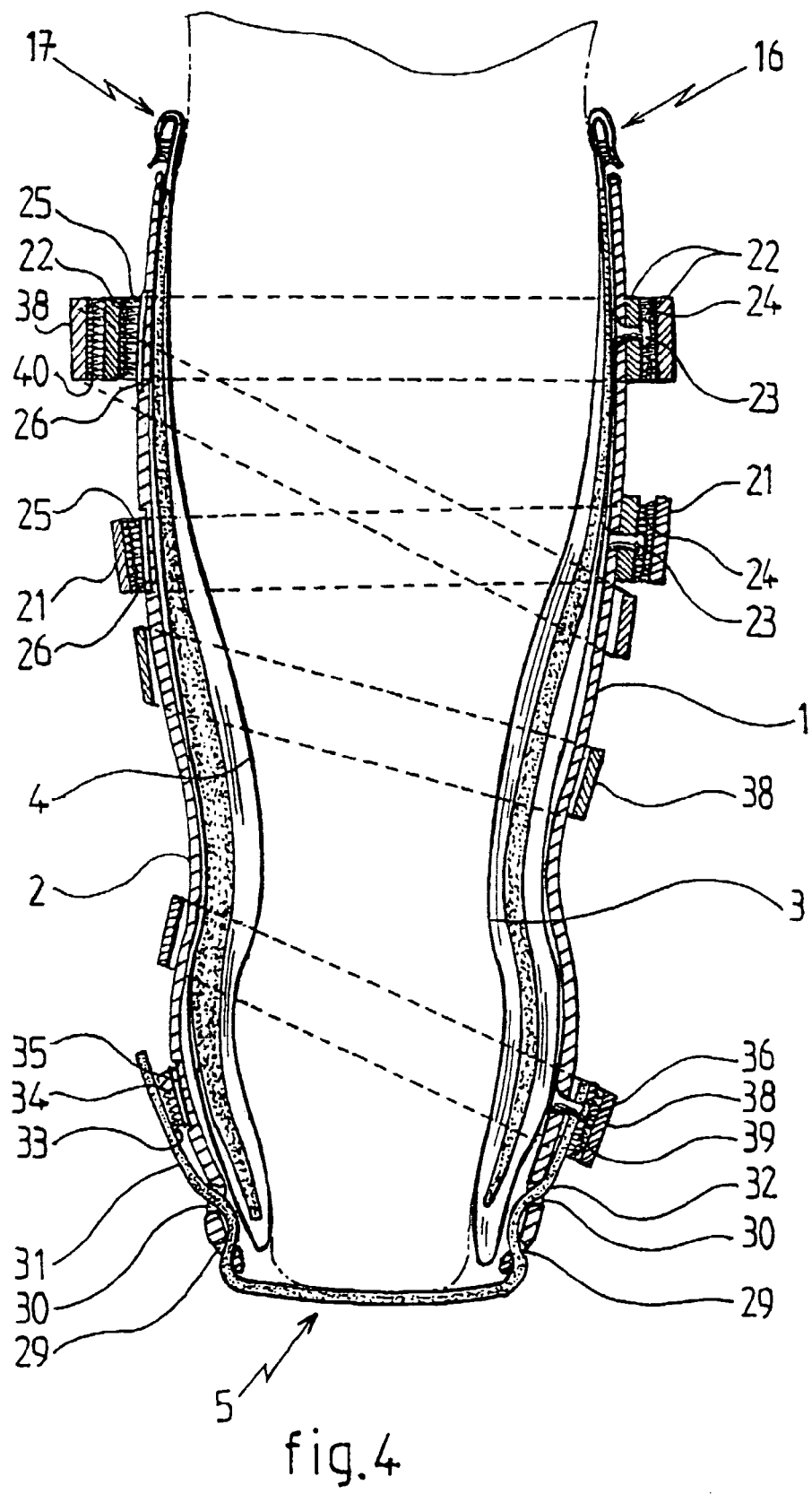

| | | | |
|---|---|---|---|
| 5,713,837 A | 2/1998 | Grim et al. | |
| 5,716,335 A | 2/1998 | Iglesias et al. | |
| 5,951,504 A * | 9/1999 | Iglesias et al. | 602/27 |
| 7,018,351 B1 * | 3/2006 | Iglesias et al. | 602/27 |

FOREIGN PATENT DOCUMENTS

| | | |
|---|---|---|
| WO | WO 87 03471 | 6/1987 |
| WO | WO 92/15262 | 9/1992 |

* cited by examiner

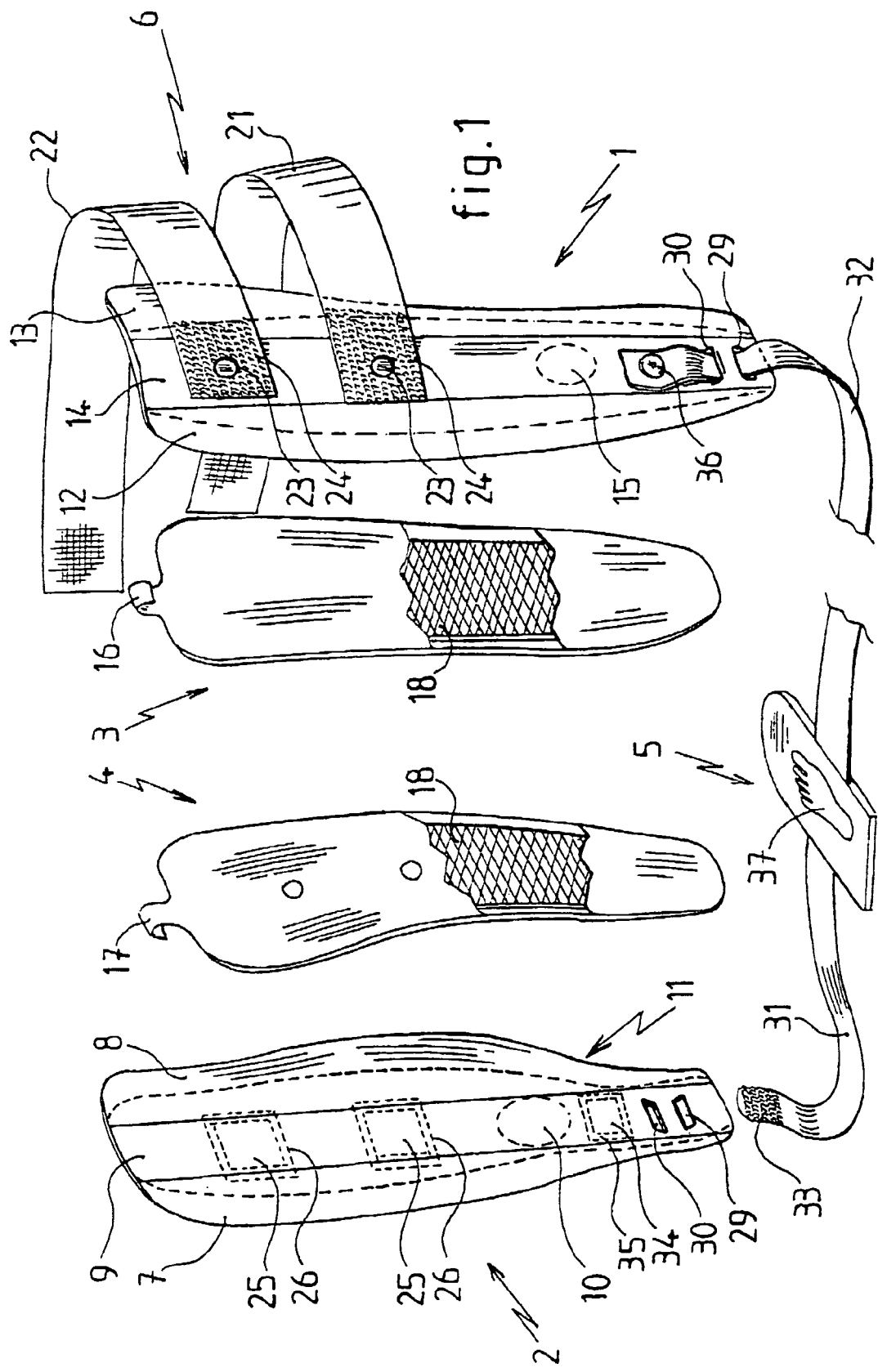

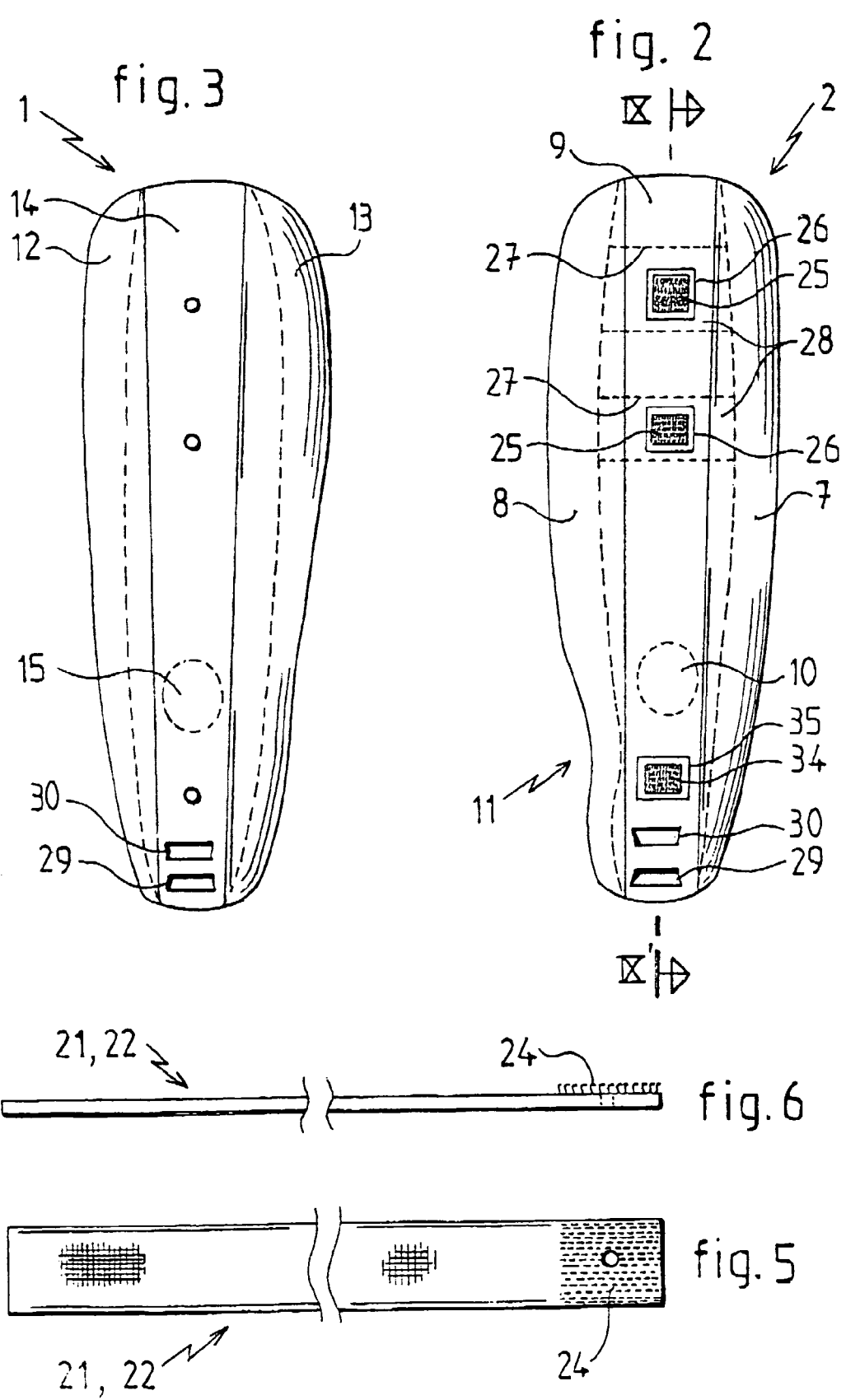

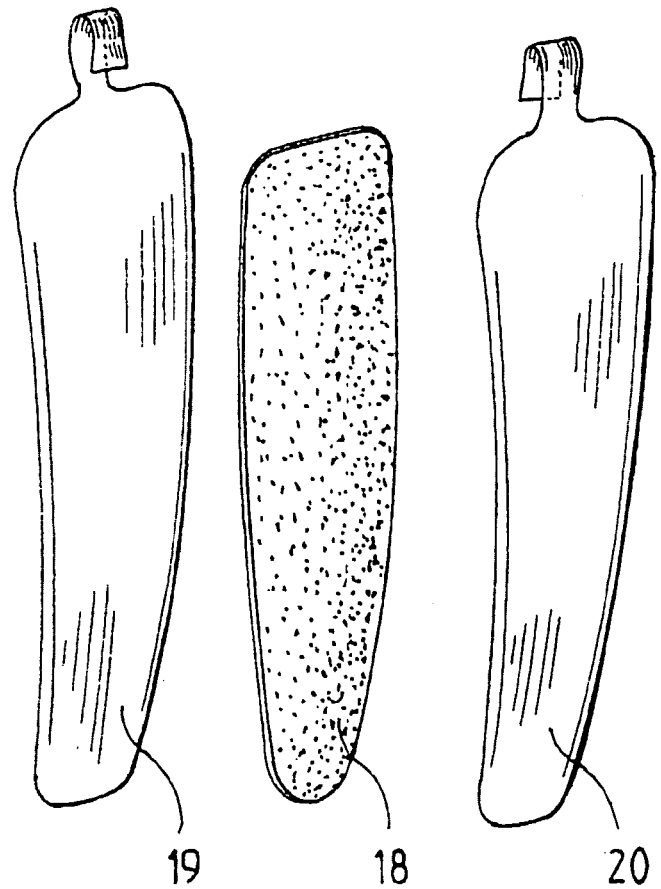
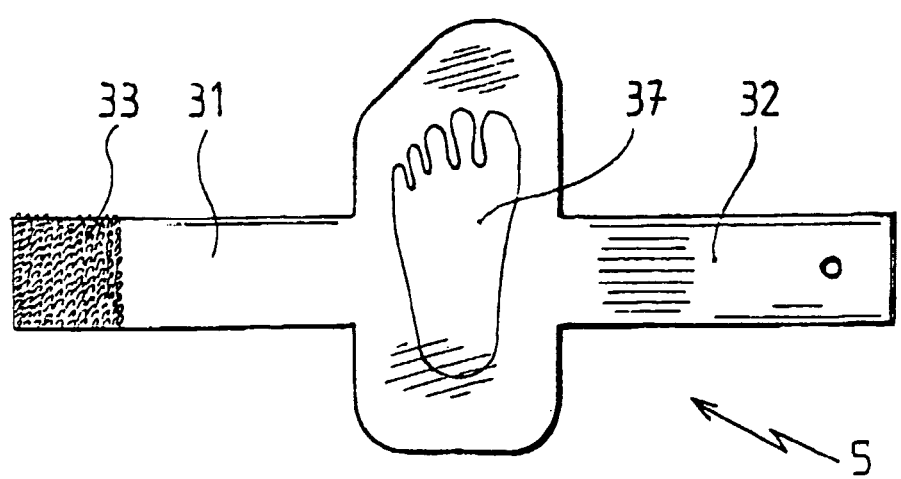

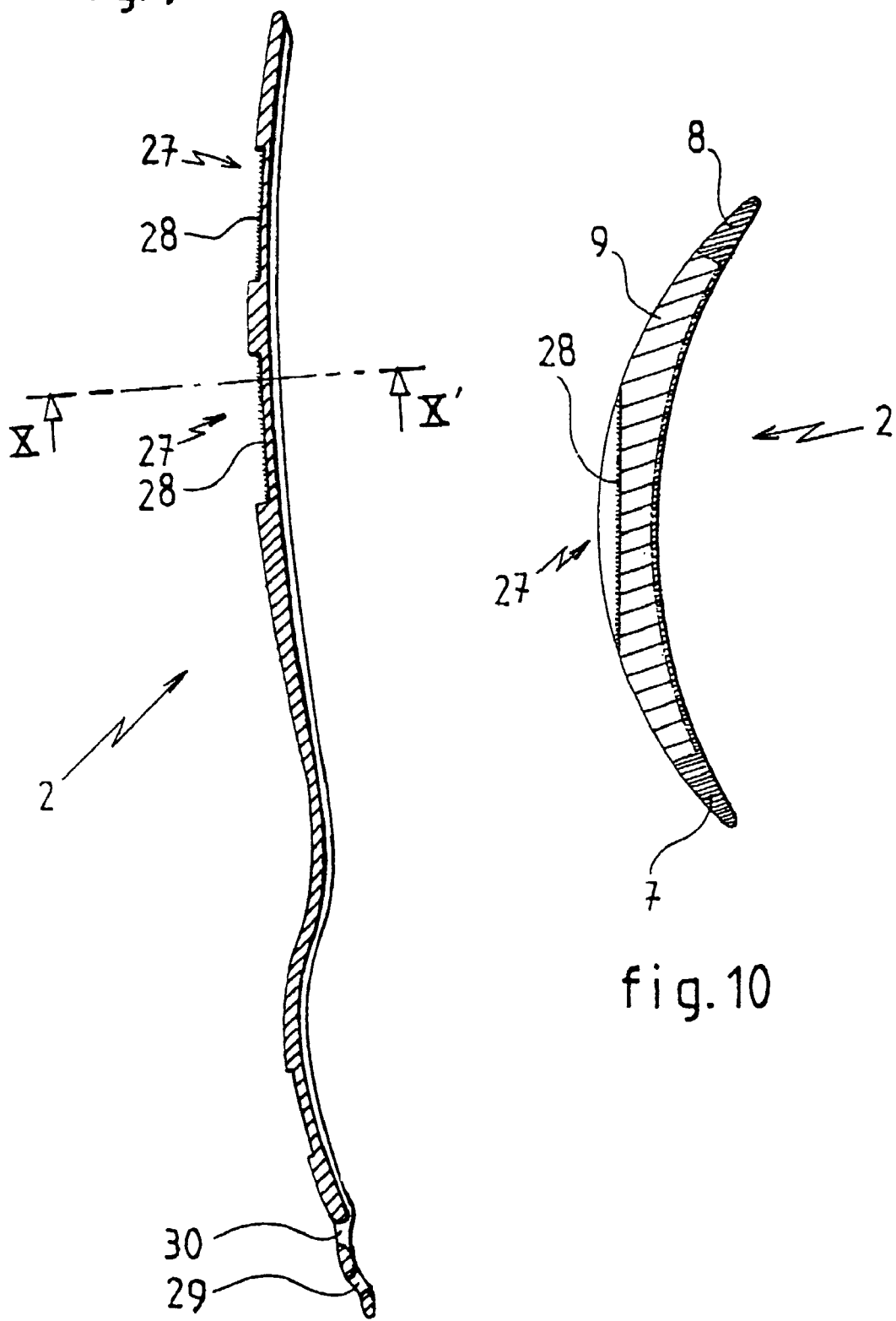

SPLINT FOR A JOINT CONNECTION AND METHODS FOR PRODUCTION OF SUCH A SPLINT

This invention relates to a splint for a joint between two members of a human or animal body, for example such as the ankle, knee or elbow, composed of at least two rigid and globally concave shells that can be positioned on each side of the joint, resting on the said joint, comprising means of avoiding an injury to the oedematous tissue that developed subsequent to a severe or minor sprain of the said joint.

In the field of traumatology, particularly in sport, ankle orthoses, commonly called splints are well known to avoid foot eversion and inversion movements while allowing normal bending of the foot, either to prevent a severe or minor sprain of the ankle, for example while practicing a sport, or to encourage resorption of an oedema resulting from a severe sprain and located around the ankle. These splints are usually composed of two rigid and globally concave shells that can be positioned on each side of the ankle, applying pressure on the said ankle, and comprising a chamber made of a flexible plastic material that can be pressurised by any appropriate means, on each of their inner faces, in other words on their concave faces. These chambers are placed on the inner face of each shell to supply a supporting cushion between each shell and the ankle, and they cover at least part of the inner face of each shell, such that during every step, these chambers compress the oedematous tissues creating a massage effect that contributes to a fast disappearance of oedemas. Furthermore, the splint comprises means of holding the said shells in position on each side of the joint composed of fabric strap surrounding the said shells of the splint.

This type of splint is described in European patent EP 0 252 121 deposited by the AIRCAST company, and concerning an ankle splint. This splint is composed of an outer envelope comprising two rigid and concave shells that can be positioned on each side of the ankle, and a base that is also rigid and can be positioned under the heel. The base comprises two tabs made from a fabric strap extending on each side of the said base and comprising loops on their outer faces, on each of their corresponding ends, capable of cooperating with "velcro" (registered trademark) type hooks moulded in the inner surface of each shell just above a globally rectangular horizontal slot located at the lower end of each shell, each tab being inserted in the slot in its corresponding shell from the outside of the shell towards the inside. The splint also comprises a first and a second chamber that can be pressurized to provide a support cushion between each shell and the ankle, the second chamber extending along the inner part of the first chamber close to the base. Furthermore, the splint comprises means of holding the shells in contact with the leg such that the pressure applied by the second chamber in contact with the ankle is relatively higher than the pressure applied on the leg by the part of the first chamber extending above the second chamber.

This type of splint has the disadvantage of having rigid edges that can bear on the oedematous tissue of the ankle causing inconvenience and pain due to the pressure applied by the rigid edges of the shells. Furthermore, the tabs on the base of the splint are fixed to the inner walls of the shells, therefore it is necessary to remove the entire splint to access the said tabs and adjust the height of the shells with respect to the base correctly, with the result that the splint is badly positioned most of the time, which is very uncomfortable for persons wearing these splints.

In order to overcome these disadvantages, splints have been conceived composed of a central rigid shell provided with linings along its longitudinal edges made from a resilient material; for example, this is the case of American patent U.S. Pat. No. 5,716,335. These linings are made of rubber or a similar material and are glued onto the longitudinal edges of the rigid shell that includes grooves to enable mechanical coupling of linings with the central rigid shell made of high density polyethylene (HDPE), nylon or nylon with a glass filler marketed by the DUPONT Company (registered trademark).

The linings of these splints have the disadvantage that they can detach, or even tear off in the case of prolonged and repeated use of these splints, thus making them completely inefficient. Furthermore, friction between the rubber and the skin of a patient wearing the splint barefoot are particularly uncomfortable and can cause burns.

Therefore one of the purposes of this invention is to overcome this disadvantage by proposing a splint for a joint between two members of a human or animal body, for example such as the ankle, with a simple design and that can avoid an injury to the oedematous tissue that developed subsequent to a severe or minor sprain of the said joint.

According to the invention, this is achieved by making a splint for a joint between two members of a human or animal body, for example such as the ankle, knee or elbow, composed of at least one rigid and globally concave shell that can be positioned around the joint, bearing on the said joint, and comprising a chamber made of a flexible plastic material that can be pressurized by any appropriate means, placed on the inner face of the shell, in other words the concave face, to provide a support cushion between the said shell and the joint, and covering at least part of the inner face of the shell, the said splint comprising means of holding the said shell in position around the joint; this splint is remarkable in that the shell is composed of a single element comprising at least one flexible area made from a styrene ethylene butylene styrene (SEBS) block copolymer chemically bonded to the rigid part of the shell to avoid any injury to the oedematous tissue that developed subsequent to a severe or minor sprain of the said joint.

According to one essential characteristic of the splint according to the invention, the shell is rigid in the central part and flexible on each of its longitudinal edges.

It is quite obvious that since the edges of the shells are flexible, they apply a lower pressure on the oedematous tissue resulting from a severe or minor sprain during bending of the foot, thus facilitating fast resorption of the oedema. Moreover, apart from the fact that SEBS is a pleasant material to touch, it improves the feeling of comfort for a user wearing the splint barefoot, the shell being made in a single part, in other words from a single mould, the flexible part of the shell does not tear off unlike devices according to prior art.

Another purpose of the invention relates to a method of manufacturing the shell(s) of a splint for a joint connecting two members of a human or similar body, for example such as the ankle, knee or elbow, composed of at least one rigid and globally concave shell, that can be positioned around the joint and bearing on the said joint.

This method consists of inserting a hot liquid synthetic material that solidifies as it cools in a mould defining the shape of the shell to be obtained, and then inserting a flexible material into the said mould in at least one area of the said mould.

According to one variant embodiment of the method according to the invention, the flexible material is added into the synthetic material.

Other advantages and characteristics will become clearer after reading the following description given as a non-limitative example, of a splint according to the invention with reference to the appended figures, wherein:

FIG. 1 is an exploded perspective view of a splint for a left ankle, according to the invention, FIG. 2 is a side view of the outer shell of the splint for an ankle, according to the invention as shown in FIG. 1, FIG. 3 is a side view of the inner shell of the splint for an ankle according to the invention as shown in FIG. 1, FIG. 4 is a front sectional view of the ankle splint in position on the ankle of a person, FIG. 5 is a plan view of a strap forming means of holding the shells with the splint according to the invention in position on each side of the ankle, FIG. 6 is a side view of the strap shown in FIG. 5, FIG. 7 is an exploded perspective view of a chamber that can be pressurised in order to form a support cushion between each shell and the ankle, FIG. 8 is a top view of the base of the ankle splint according to the invention, FIG. 9 is a sectional view along the IX-IX' axis of a variant embodiment of the outer shell of the splint according to the invention shown on FIG. 2, FIG. 10 is a sectional view along the X-X' axis of the variant embodiment of the shell of the splint according to the invention shown in FIG. 9.

In this non-limitative example, we will describe an ankle splint according to the invention adapted for the left ankle of a person.

The ankle splint is shown vertically on FIG. 1, and is composed of two rigid and globally concave shells, a first so-called inner shell 1 that can be positioned on the inner side of the ankle and a second so-called outer shell 2 that can be positioned on the outer side of the said ankle.

Each inner and outer shell 1 and 2 comprises chambers 3 and 4 on each of their corresponding inner walls, in other words their concave parts that face the ankle when the splint is positioned around the ankle, the chambers being made of a flexible plastic material that can be pressurised by any appropriate means, for example a pipette, placed on the inner wall of each shell 1 to 2 to provide a support cushion between each shell and the ankle. The splint also comprises a base 5 on which the heel applies pressure and means 6 of holding the said shells 1 and 2 in position on each side of the ankle, the base 5 and means 6 will be described more precisely later on.

With reference to FIGS. 1 and 2, the outer shall 2 comprises flexible areas 7 and 8 along its longitudinal edges, in order to avoid an injury to the oedematous tissue subsequent to a severe or minor sprain of the ankle, the flexible areas 7 and 8 applying lower pressure on the oedematous tissue during bending of the foot, which facilitates fast resorption of the oedema. Note that the central part 9 of the outer shell 2 extending from its lower end to its upper end is rigid; in this context, the thickness of the central part of the outer shell is preferably greater than the thickness of the flexible areas 7 and 8 of the said outer shell 2. Accessorily, the central part of the outer shell 2 comprises a globally circular flexible area 10 corresponding to an area of the said outer shell that applies pressure on the medial malleolus of the ankle that forms a protuberance from this joint. The flexible areas 7, 8 or 10 are made partly of a flexible material, preferably SEBS, in other words styrene ethylene butylene styrene block copolymer (thermoplastic elastomer) mixed with a rigid synthetic material such as polypropylene copolymer (PPc) or polyamide 6 (PA 6), from which the rigid part of the outer shell 2 is made.

According to one variant embodiment of the ankle splint according to the invention and with reference to FIG. 10, the flexible areas 7, 8 or 10 are made by adding a synthetic material for example such as PPc or PA6, as a hot liquid that solidifies as it cools in a mould defining the shape of the shell so as to obtain the rigid central part 9, and then by adding a flexible material, for example such as SEBS, into the said mould in the part of the mould corresponding to the inner part of the shell such that the flexible material extends on each side of the rigid central part 9 to form flexible areas 7 and 8 on the inner wall of the said shell. Note that SEBS is a material with a particularly pleasant feel and it improves the feeling of comfort, for example for a user wearing the splint barefoot.

Furthermore, with reference to FIGS. 1 and 2, the outer shell 2 comprises a scalloped recess 11 along its front side edge, in other words the vertical side edge at the right of FIGS. 1 and 2 and close to its lower edge, to prevent any pressure from the side edge in contact with the bump and on the top of the foot during bending of the leg.

With reference to FIGS. 1 and 3, in the same way as above, the inner shell 1 comprises a flexible area 12 and 13 delimited by dashed lines, along its longitudinal edges. The central part 14 of the inner shell is rigid and in this respect is thicker than the flexible areas. Accessorily, the inner shell 1 comprises a flexible area 15 in its rigid central part 14 corresponding to the area in which the inner shell 1 applies pressure on the medial malleolus of the ankle.

With references to FIGS. 1, 4 and 7, chambers 3 and 4 are solidarised to the inner walls of the inner shell 1 and outer shell 2 by any appropriate means such as glue or Velcro (registered trademark) type fastening means such that it covers the inner wall of each of the shells 1 and 2 so as to provide a support cushion between each shell 1 and 2 and the ankle. The chambers 3 and 4 have a globally triangular shape and include valves 16 and 17 respectively and can cooperate with any appropriate means, such as a pipette consisting of a flexible tube, so as to pressurise the said chambers 3 and 4, the pressure being applied by blowing into the pipette inserted in valve 16 or 17 of the chamber 3 or 4. In a particularly advantageous manner, each chamber 3 or 4 comprises a porous compressible element 18 placed on the inside of each of the chambers 3 and 4, practically filling the inner volume of each of the said chambers 3 and 4 when these chambers are not pressurised. The porous compressible element 18 is preferably composed of foam with slow resilience, for example such as low strength polyether foam 1.50 LR3 marketed by the TRAMICO company. A low resilience polyether foam is a foam that is deformed under the effect of pressure and returns very slowly to its initial position.

With reference to FIG. 7, the chambers 3 and 4 are obtained by thermo-welding two globally triangular sheets 19 and 20 made from a flexible plastic material such as ethyl vinyl acetylene (E.V.A.), and preferably polyurethane, thermo-welded along their edges, the porous compressible element 18 being positioned between the two sheets 19 and 20 before they are thermo-welded.

With reference to FIGS. 1 and 4, the means 6 of holding the inner shell 1 and outer shell 2 in position on each side of the ankle are composed of two velvet finish fabric straps 21, 22, a free end of which is solidarised to the outer wall of the inner shell 1 of the splint by an attachment means, for example such as a rivet 23. Each strap 21, 22 comprises male attachment means 24 solidarised to the outer face of straps 21, 22 close to the fixed edge of the inner shell, as shown in FIGS. 1, 4, 5 and 6, the said male attachment means 24 being capable of cooperating with the thin loops on the inner face of the velvet finish fabric straps 21, 22. A velvet finish fabric means a fabric with two superposed warps, one of which forms the bottom of the fabric and the other the velvet finish by thin loops on its faces. Furthermore, the loops of the velvet finish fabric of the straps 21, 22 can cooperate with the male attachment means 25 fixed to the outer wall of the second outer shell 2.

With reference to FIGS. 1, 2 and 4, the male attachment means 25 fixed to the outer wall of the outer shell 2 of the splint and capable of cooperating with the thin loops of the strap 21, 22 are positioned in the corresponding two recesses 26 formed on the outer wall of the outer shell 2 such that the attachment means 25 are flush with the surface of the said outer wall, the said male attachment means 25 advantageously being glued to the bottom of the recesses 26.

Furthermore, the male attachment means consist of hooks and the female attachment means consist of loops, the said hooks being capable of cooperating with the loops and vice versa to form a Velcro (registered trademark) type attachment.

As shown in FIGS. 2 and 9, and according to one particularly advantageous execution of the splint according to the invention, the male attachment means 25 are replaced by two globally rectangular transverse grooves 27, shown in chain dotted lines in FIG. 2, with a straight section, extending perpendicular to the longitudinal edges of the outer shell 2 in the central part 9 of the said shell 2 and for which the bottom 28 has a rough surface. Thus, the grooves 27 that hold the fabric straps 21, 22 in position and that cannot slide along the longitudinal centreline of the outer shell 2 and the rough surface of the bottoms 28 of the said grooves 27 prevent any transverse sliding of the straps 21, 22, by cooperating with the thin loops of the said straps.

It is quite obvious that the rough surface can be made from any anti-slip material or similar material obtained either when moulding the shell 2, or by gluing the said material on the bottoms 28 of the grooves 27.

With reference to FIGS. 1 to 4, each shell 1, 2 comprises two globally rectangular parallel horizontal slots 29 and 30 at its lower end, one 30 placed above the other 29, into which the fabric tabs 31 and 32 extending on each side of the base 5 and that can be positioned under the heel can be inserted. Each tab 31, 32 is inserted passing under a shell 1, 2, by inserting its free end in the first lower slot 29 from the outside towards the inside of the shell 1, 2, and then by inserting the said end into the second upper slot 30 from the inside towards the outside of the said shell 1, 2, before solidarising its free end on the outer wall of the shell 1, 2 immediately above the slots 29, 30. In this particular example embodiment, the first tab 31 is made of a velvety fabric and it comprises thin loops 33 on its inner face, in other words the face in contact with the outer wall of the shells 1, 2, capable of cooperating with male attachment means 34 placed on the outer wall of the outer shell 2 just above the slots 29, 30. The said male attachment means 34 are advantageously positioned in a recess 35 formed on the outer wall of the shell 2 such that the male attachment means 34 are flush with the surface of the said outer wall.

The free end of the second tab 32 is fixed to the outer wall of the inner shell 1 by a rivet 36.

It is obvious that the second tab 32 may also comprise thin loops on its inner face that can cooperate with male attachment means advantageously placed in a hollow formed on the outer wall of the inner shell immediately above the slots 29, 30.

Accessorily, it is observed that the part of the shells 1 and 2 extending between the slots 29 and 30 is slightly set back such that the tabs 31 and 32 extending between the said slots 29 and 30 on the inner face of the shells 1 and 2 are flush with the inner wall of the said shells thus preventing any extra thickness that would hinder the user.

Furthermore, with reference to FIGS. 1 and 8, the base 5 is generally in the shape of a foot and it comprises a stylised representation 37 of a left foot on the upper face of the base 5, in other words the face of the base 5 facing the heel, such that the user can easily identify which splint he should place on his left ankle.

It is quite obvious that the base 5 of the splint corresponding to the right ankle will be marked with a stylised representation of a right foot on its upper face.

Accessorily, with reference to FIG. 4, the splint advantageously comprises a velvety fabric "strapping" 38 comprising male attachment means 39 and 40 on one of its faces, placed at the corresponding free ends of the said "strapping" 38, and capable of cooperating with the thin velvety fabric loops on the outer face of the tab 34 and the outer face of the strap 22 or 21, the strapping 38 being wound around the shells 1, 2 from their lower ends as far as means 6 to hold the shells 1, 2 in position on each side of the ankle. It will be observed that the term "strapping" means application of a retaining strap around a member of the body. This strapping 38 pulls the foot inwards while walking, to counteract the tendency of the foot to pivot outwards due to the flaccidity of the ankle tendons caused by the severe sprain.

Finally, it is obvious that the ankle splint according to the invention can be adapted to all joints of a human or animal body, for example such as the knee, elbow or wrist, that such splints only comprise a single shell, and that the examples that have just been described are simply particular illustrations and in no way limit the fields of application of the invention.

The invention claimed is:

1. A splint for a joint between two members of a human or animal body, composed of
    at least one rigid and globally concave shell (1, 2) that can be positioned around the joint, resting on the joint, wherein the concave shell comprises a chamber (3, 4) made of a flexible plastic material that can be pressurised by any appropriate means, on a concave inner face of the at least one concave shell, wherein the chamber is placed on the concave inner face of the concave shell (1, 2) to supply a supporting cushion between the concave shell (1, 2) and the joint, and the chamber covers at least a part of the concave inner face of the concave shell (1, 2); and
    means (6) of holding the at least one concave shell (1, 2) in position around the joint, wherein the at least one concave shell (1, 2) is composed of a single element comprising a rigid part and at least one flexible area (7, 8; 12, 13) to avoid any injury to the oedematous tissue that developed subsequent to a severe or minor sprain of the joint, wherein the flexible area is made from a styrene ethylene butylene styrene (SEBS) block copolymer mixed with a rigid synthetic material from which the rigid part is made so that the shell is made from a single mould wherein the flexible area is chemically bonded to the rigid part of the shell (1, 2).

2. The splint according to claim 1, wherein the rigid part of the at least one concave shell (1, 2) is obtained from polypropylene copolymer (PPc).

3. The splint according to claim 1, wherein the rigid part of the at least one concave shell (1, 2) is obtained from polyamide 6 (PA 6).

4. The splint according to claim 1, wherein the at least one concave shell (1, 2) is rigid at a central part (9, 14) and flexible (7, 8; 12, 13) along each of the longitudinal edges of the at least one concave shell.

5. The splint according to claim 1, wherein the at least one concave shell (1, 2) comprises at a central part (9, 14) a flexible area (10, 15) corresponding to an area of the at least one concave shell (1, 2) that rests on a protuberance of the joint.

6. The splint according to claim 1, further comprised of a porous compressible element (18) placed on the inside of each chamber (3,4), filling the inner volume of each of the chambers (3,4) when these chambers are not pressurized.

7. The splint according to claim 6, wherein the porous compressible element (18) is composed of a foam with a slow resilience.

8. The splint according to claim 1, wherein the means (6) of holding the at least one concave shell in position around the joint is comprised of at least two velvet finish fabric straps (21, 22) formed from a fabric comprising thin loops on the faces of the fabric, wherein each of the velvet finish fabric straps (21, 22) having firstly a free end solidarised to the outer face of the concave shell (1, 2) of the splint by an attachment means the fabric straps (21, 22) being capable of cooperating with a first male attachment means (25) fixed to the outer face of the concave shell(1, 2) and secondly having a second male attachment means (24) positioned on the outer face of the strap (21, 22) at a fixed end of the at least one concave shell (1, 2) and capable of cooperating with the thin loops of the inner face of the velvet finish fabric straps(21, 22).

9. The splint according to claim 8, wherein the first male attachment means (25) consists of at least two globally rectangular transverse grooves(27) with a straight section, extending perpendicular to the longitudinal edges of the concave shells (1, 2) in the central part (9, 14) of the at least one concave shells (1, 2) and for which a bottom (28) of the at least one concave shell has a rough surface.

10. The splint according to claim 8, wherein the first male attachment means (25) are positioned in a recess (26) formed on the outer wall of the at least one concave shell (1, 2) such that the first male attachment means (25) are flush with the surface of the outer wall.

11. The splint according to claim 10, wherein the first male attachment means (25) of the outer face of the concave shell (1, 2) of the splint are glued to the bottom of the recesses (26) formed on the outer wall of the at least one concave shell (1, 2).

12. The splint according to claim 8, wherein the first and second male attachment means (24, 25) consists of hooks capable of cooperating with the thin loops of the velvet finish fabric straps (21, 22).

13. The splint of claim 1, wherein comprising at least two concave shells (1, 2) capable of being positioned on each side of an ankle.

14. The splint according to claim 13, wherein each concave shell (1, 2) comprises two globally rectangular horizontal slots (29, 30) at a lower end of the concave shells, one globally (30) placed above the other globally rectangular horizontal slots (29), and into which the velvet finish fabric tabs (31, 32) extend on each side of a base (5) and can be positioned under a heel, each velvet finish fabric tab (31, 32) inserted such that each velvet finish fabric tab passes under one of the concave shells (1, 2) by inserting a free end in the lower globally rectangular parallel horizontal slot (29) from the outside towards the inside of the concave shell (1, 2), and then by inserting the free end into the upper globally rectangular horizontal slot (30) from the inside towards the outside of the concave shell (1, 2), before solidarising its free end on the outer wall of the concave shell immediately above the globally rectangular parallel horizontal slots (29, 30).

15. The splint according to claim 14, wherein the free end of at least one velvet finish fabric tab (31, 32) comprises thin loops (33) capable of cooperating with a third male attachment means (34) placed on the outer wall of the concave shells (1, 2) just above the globally rectangular parallel horizontal slots (29, 30), on its inner face, such that the inner face is in contact with the outer wall of the concave shells (1, 2).

16. The splint according to claim 15, wherein the third male attachment means (34) is positioned in a recess (35) formed on the outer wall of the concave shells (1, 2) such that the third male attachment means (34) is flush with the surface of the outer wall.

17. The splint according to claim 14, wherein the base (5) is generally in the shape of a foot.

18. The splint according to claim 14, further comprising a stylised representation (37) of a foot on the upper face of the base facing the heel.

19. The splint according claim 14, wherein the free end of one of the velvet finish fabric tabs (31, 32) are fixed to the outer wall of the concave shell (1, 2) by means of a rivet (36).

20. The splint according to claim 14, further comprising a velvety fabric "strapping" (38) comprising a fourth male attachment means (39, 40) on one of the velvety fabric strapping faces, placed at the corresponding free ends of the velvety fabric "strapping" (38), and capable of cooperating with the thin velvety fabric loops on the outer face of the tab (34) and the outer face of the strap the velvety fabric "strapping" (38) being wound around the concave shells (1, 2) from their lower ends as far as the means of holding the concave shells (1, 2) in position on each side of the ankle.

21. A method for manufacturing shells (1, 2) of a splint for a joint between two members of a human body composed of at least two rigid and globally concave shells (1, 2) that can be positioned on each side of the joint and can apply pressure on the joint comprising:
- inserting a hot liquid synthetic material that solidifies as it cools in a mould defining the shape of the concave shells (1, 2) wherein the solidified structure defines a rigid part; and
- inserting a flexible material into the said mould in at least one area of the mould such that a flexible part is formed and chemically bonded to the rigid part of the concave shells.

22. The method for manufacturing shells in the splint for the joint according to claim 21, wherein the flexible material is inserted into the synthetic material.

* * * * *

UNITED STATES PATENT AND TRADEMARK OFFICE
CERTIFICATE OF CORRECTION

PATENT NO. : 7,662,117 B2  
APPLICATION NO. : 10/511377  
DATED : February 16, 2010  
INVENTOR(S) : Jean-Paul Parizot Page 1 of 1

It is certified that error appears in the above-identified patent and that said Letters Patent is hereby corrected as shown below:

Column 7, Claim 14, line 50, after "rectangular" insert -- parallel --

Column 7, Claim 14, line 51, after "globally" insert -- rectangular parallel horizontal slot --

Column 7, Claim 14, line 52, after "rectangular" insert -- parallel --

Column 8, Claim 14, line 4, after "rectangular" insert -- parallel --

Signed and Sealed this  
Twenty-fourth Day of May, 2011

David J. Kappos  
*Director of the United States Patent and Trademark Office*